United States Patent [19]

Gschwend

[11] 4,022,801
[45] May 10, 1977

[54] PYRAZOLOBENZAZEPINES

[75] Inventor: Heinz Werner Gschwend, New Providence, N.J.

[73] Assignee: Ciba-Geigy Corporation, Ardsley, N.Y.

[22] Filed: May 5, 1975

[21] Appl. No.: 574,211

Related U.S. Application Data

[63] Continuation-in-part of Ser. No. 475,474, June 3, 1974, Pat. No. 3,947,585.

[52] U.S. Cl. .......................... 260/310 R; 260/311; 260/295 T; 260/295.5 S; 424/273
[51] Int. Cl.² ....................................... C07D 471/00
[58] Field of Search .......... 260/310 R, 311, 295 T, 260/295.5 S; 424/273

[56] References Cited
FOREIGN PATENTS OR APPLICATIONS
2,524,048  1/1976  Germany

*Primary Examiner*—Donald B. Moyer

*Attorney, Agent, or Firm*—Joseph G. Kolodny; Theodore O. Groeger; John J. Maitner

[57] ABSTRACT

6-Aryl-1- or 2H,4H-pyrazolo[4,3-d](2)-benzazepines, e.g. those of the formula

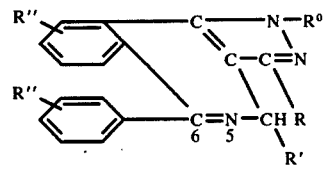

R = H or alkyl
R° = H, alkyl, (HO, alkoxy, amino)-alkyl, aralkyl, aryl or acyl,
R' = H, OH or alkyl
R" = H, alkyl, alkoxy, halo or CF₃

N-oxides thereof or therapeutically useful acid addition salts of such compounds exhibit antianxiety and antidepressant effects.

5 Claims, No Drawings

PYRAZOLOBENZAZEPINES

CROSS-REFERENCE TO RELATED APPLICATION

This is a continuation-in-part of application Ser. No. 475,474, filed June 3, 1974, now U.S. Pat. No. 3,947,585.

SUMMARY OF THE INVENTION

The present invention concerns and has for its object the provision of new 6-aryl-1 or 2H,4H-pyrazolo[4,3-d](2)benzazepines, preferably of those corresponding to the tautomers of Formulae I and II

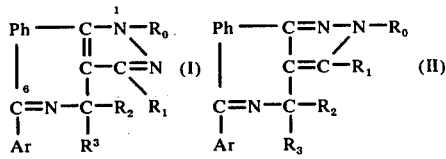

wherein Ph is a 1,2-phenylene radical, Ar is a momocyclic, carbocyclic aryl radical, $R_o$ is hydrogen, lower alkyl, (hydroxy, lower alkoxy or Am)-$C_mH_{2m}$, Ar-$C_nH_{2n}$, lower alkanoyl, lower alkoxycarbonyl, AmCO, AmCS or cyano, wherein Am is an amino group, m is an integer from 1 to 7, n is an integer from 0 to 7, each or $R_1$ and $R_2$ is hydrogen or lower alkyl, and $R_3$ is hydrogen, lower alkyl, hydroxy or lower alkanoyloxy; or N-oxides thereof, or salts, particularly therapeutically useful acid addition salts of such compounds; as well as of corresponding pharmaceutical compositions and of methods for the preparation and application of these products, which are useful antianxiety and antidepressant agents.

DESCRIPTION OF THE PREFERRED EMBODIMENTS

The 1,2-phenylene radical Ph, as well as the aryl radical Ar, are unsubstituted or substituted by one or more than one, preferably by one or two, of the same or different substituents selected from the group consisting of lower alkyl, e.g. methyl, ethyl, n- or i-propyl or -butyl; etherified or esterified hydroxy, such as lower alkoxy, e.g. methoxy, ethoxy, n- or i-propoxy or -butoxy; or halo, e.g. fluoro, chloro or bromo; or trifluoromethyl. The term "lower", referred to above and hereinafter in connection with organic radicals or compounds respectively, defines such with up to 7, preferably up to 4, carbon atoms.

Preferred 1,2-phenylene radicals Ph are 1,2-phenylene, (lower alkyl)-1,2-phenylene, (lower alkoxy)-1,2-phenylene, (halo)-1,2-phenylene or (trifluoromethyl)-1,2-phenylene and preferred aryl radicals Ar are phenyl, (lower alkyl)-phenyl, (lower alkoxy)-phenyl, mono- or di-(halo)-phenyl or (trifluoromethyl)-phenyl.

The radical $R_o$ preferably represents hydrogen, lower alkyl or Ar-$C_nH_{2n}$, wherein n is an integer from 0 to 7, preferably 1 to 4. It may also represent (hydroxy, lower alkoxy or Am)-$C_mH_{2m}$ wherein m is a integer from 1 to 7 and Am is an open or cyclic amino group exemplified by unsubstituted amino, mono- or di-lower alkylamino, lower alkyleneimino or mono-aza-, mono-oxa- or monothiaalkyleneimino, wherein the additional nitrogen, oxygen or sulfur atom is separated from the imino-nitrogen by at least 2 carbon atoms. Amino groups are e.g. amino, mono- or di-(methyl, ethyl, n- or i-propyl or -butyl)-amino; pyrrolidino, piperidino or hexamethylenedimino; piperazino, 4-(lower alkyl, e.g. methyl or ethyl)-piperazino; morpholino or thiamorpholino. Preferred amino groups Am are mono- or di-lower alkylamino, pyrrolidino, piperidino, piperazino, 4-(lower alkyl)-piperazino or morpholino. Other groups $R_o$ are lower alkanoyl, e.g. formyl, acetyl, propionyl or pivalyl, lower alkoxycarbonyl, e.g. methoxy-, ethoxy-, n- or i-propoxy- or -butoxy-carbonyl and AmCO or AmCS, in which Am has the above-given meaning.

The radicals $R_1$, $R_2$ and $R_3$ represent preferably a hydrogen atom, but also lower alkyl, above all methyl; $R_3$ also stands for hydroxy or lower alkanoyloxy, e.g. acetoxy, propionyloxy or pivalyloxy.

The compounds of the invention exhibit of the invention exhibit valuable pharmacological properties, for example, imipramine-type antidepressant and especially antianxiety effects of long duration. This can be demonstrated in animal tests, using advantageously mammals, such as mice, rats or monkeys, as test objects. The compounds of the invention can be applied to the animals enterally, e.g. orally, or parenterally, such as subcutaneously or intaperitoneally, e.g. in the form of aqueous solutions or starchy suspensions. The dosage may range between about 0.1 and 300 mg/kg/day, preferably between about 1 and 100 mg/kg/day, advantageously between about 2 and 20 mg/kg/day. An antidepressant effect is observed, for example, in the amphetamine interaction test (P. Carlton, psychopharmacologia 1961, Vol II, p. 364) performed with male albino rats, which are trained to press a bar every 30 seconds, in order to avoid an electric shock applied through the floor grid. In case the animals receive i.p. 0.25 mg/kg/day of amphetamine, their performing rate for avoiding said shocks during a test period or about 4–5 hours is slightly higher than that of placebo (saline) treated animals. In case the animals receive the compounds of the invention (or imipramine for control purposes) in the above-mentioned doses, preferably at 5 or 10 mg/kg/day i.p. and about 45 minutes later the amphetamine, their rate of avoiding the shocks is highest, as compared with that of rates receiving a) saline alone, b) saline and amphetamine, or c) the compounds of the invention and saline. Primarily, however, the compounds of the invention exhibit antianxiety effects in rats or squirrel monkeys, advantageously at dosages between about 2 and 20 mg/kg/day. Accordingly, they reduce acquired fear or anxiety associated with a psychological conflict. It is established by simultaneously rewarding with food and punishing with electric shock all lever-pressing responses of the animals made in the presence of a discriminative tone stimulus. For example, rats first learn to press a lever to obtain a milk reward, which is delivered on the average of once per two minutes. After this schedule, which lasts fifteen minutes, a tone stimulus of three minute duration is presented. This stimulus signals a change from a variable interval schedule of reinforcement, to a continuous reinforcement schedule (CRF). During the CRF schedule, all lever responses not only produce milk rewards but also an electric shock to the animals' feet. During the period in which a shock accompanies the food reward, the tone stimulus produces a suppression of all lever pressing responses. Thus, for example, administration of 8-chloro-6-(2-fluorophenyl(-1-methyl-1H, 4H-pyrazolo[4,3-d](2)benzazepine or salts thereof, a characteristic compound of the invention, applied at about 5 mg/kg/day intraperitoneally to rats or orally to squirrel monkeys, reinstate these responses, indicating that the animals tolerate more shocks in obtaining the food reinforcement. Accordingly, the compounds of the invention are useful antidepressants and in combatting anxiety problems. Moreover, they are also valuable intermediatess in the preparation of other useful products, especially of pharmacologically active compounds.

Particularly useful are compounds of Formulae I and II, in which Ph is 1,2-phenylene, (lower alkyl)-1,2-phenylene, (lower alkoxy)-1,2-phenylene, (halo)-1,2-phenylene or (trifluoromethyl)-1,2-phenylene, Ar is H-Ph, $R_o$ is hydrogen, lower alkyl, (hydroxy, lower alkoxy or Am)-$C_mH_{2m}$, Ar-$C_nH_{2n}$ lower alkanoyl, lower alkoxycarbonyl, AmCO or AmCS, wherein Am is amino, mono- or di-lower alkylamino, or five to seven ring-membered lower alkyleneimino, m is an integer from 2 to 4, and n an integer from 0 to 4, each of $R_1$ and $R_2$ is hydrogen or lower alkyl, and $R_3$ is hydrogen, lower alkyl, hydroxy or lower alkanoyloxy, an N-oxide thereof or therapeutically useful acid addition salts of such compounds.

Preferred compounds of the invention are those of Formulae I and II, wherein Ph is 1,2-phenylene, (alkyl)-1,2-phenylene or (halo)-1,2-phenylene, Ar is H-Ph, $R_o$ in compounds of the formula I or II is hydrogen, alkyl, 2- or 3-(hydroxy or dialkylamino)(ethyl or propyl) or H-Ph-methyl and, in addition, $R_o$ in compounds of the formula II is also alkanoyl, alkoxycarbonyl, mono- or dialkylcarbamoyl or -thiocarbamoyl each of $R_1$ and $R_2$ is hydrogen or methyl, and $R_3$ is hydrogen or hydroxy, whereby alkyl, alkanoyl or alkoxy has up to 4 carbon atoms, the 5-N-oxides thereof or the therapeutically useful acid addition salts of such compounds.

Outstanding are the compounds of Formulae III and IV

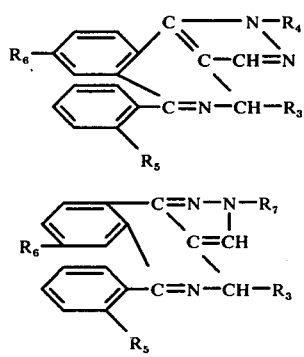

wherein $R_3$ is hydrogen or hydroxy, $R_4$ is hydrogen, alkyl with up to 4 carbon atoms, e.g. methyl, ethyl, n- or i-propyl, n-,i- or t-butyl, 2- or 3-(hydroxy, dimethylamino- or diethylamino)-(ethyl or propyl) or benzyl, each of $R_5$ and $R_6$ is hydrogen, methyl, fluoro or chloro and $R_7$ is $R_4$ or formyl, acetyl, (methoxy or ethoxy)-carbonyl, mono- or dimethyl or -ethylcarbamoyl or -thiocarbamoyl, or a therapeutically acceptable acid addition salt thereof.

The compounds of this invention are prepared according to conventional methods, for example by dehydrating compounds of Formula V

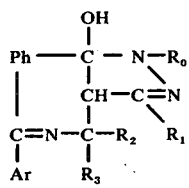

and, if desired, converting any resulting product into another compound of the invention.

Dehydration is advantageously performed by pyrolytic action at moderately raised temperatures, e.g. in the range between room temperature and the melting point of the starting material, preferably between about 50° and about 150°.

Dehydration is more easily achieved by treatment with acidic agents, advantageously mineral acids, such as hydrohalic, sulfuric or phosphoric acids, either in single- or multi-phasic media, e.g. aqueous media for said acids and water-immiscible organic solvents for the starting material.

Another process for the preparation of compounds of Formulae I and II consists in condensing compounds of Formulae Va or Vb

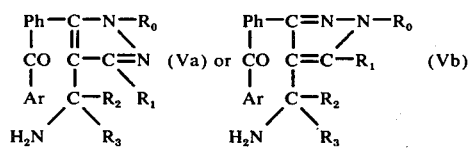

and, if desired converting any resulting product into another compound of the invention.

Said condensation is preferably performed under neutral or mildly basic conditions, for example in said water-immiscible organic solvents for the starting material Va or Vb and in the presence or absence of ammonia or other nitrogen bases, such as pyridine, mono-, di- or tri-lower alkylamine or -pyridines, at room temperature or up to about 100°.

Another procedure for the manufacture of the compounds of the formula I or II comprises oxidizing a compound of one of the formulae Vc or Vd

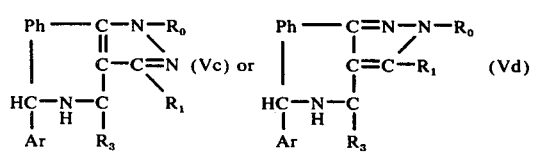

and isolating a compound of the formula I or II, and if desired, converting a resulting product into another compound of the invention.

The oxidation is preferably carried out by treatment with a heavy metal oxidizing agent, such as manganese dioxide or chromium dioxide, usually in the presence of a solvent. If necessary, a resulting mixture of compounds I or II with the corresponding isomeric compounds Ve or Vf can be separated in a conventional manner, for example by crystallization or chromatography.

An additional process for the preparation of compounds of the formulae I and II comprises isomerizing a compound of the formula

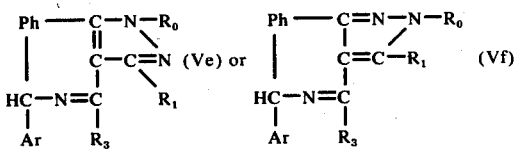

and isolating a compound of the Formula I or II, and, if desired, converting a resulting product into another compound of the invention.

The isomerization is carried out, for example, by treatment of the starting material with a strong base, such as a metal hydroxide, for example, an alkali or alkaline earth metal hydroxide, e.g. sodium hydroxide, in a solvent such as a lower alkanol, or with a metal alcoholate such as an alkali or alkaline earth metal lower alkoxide, e.g. sodium or potassium methoxide, ethoxide or tert.-hydroxide, in a solvent, such as a lower alkanol, at room temperature or as an elevated temperature. If necessary, a resulting mixture of starting materials and products is separated by conventional methods, such as crystallization, chromatography and the like.

The resulting compounds can be converted into each other according to conventional methods. For example, resulting compounds containing at least one hydrogen atom attached to an oxygen or nitrogen atom can be acylated, for example, with the use of reactive functional derivatives of the corresponding acids. such as halides or anhydrides thereof, e.g. acetyl or propionyl chloride, lower alkyl chloroformates; carbamoyl or thiocarbamoyl chlorides; acetic anhydride, ketenes, isocyanates or isothiocyanates. In addition, compounds having an N-lower alkoxycarbonyl or an N-CO-Am group may also be obtained by treatment of a resulting compound having a nitrogen atom with at least one hydrogen with phosgene, followed by reaction with a lower alkanol and Am-H, respectively. Furthermore, compounds having a nitrogen atom with at least one hydrogen can also be reacted with reactive esters of alcohols, preferably esters with strong acids, such as hydrohalic, or aliphatic or aromatic sulfonic acids, e.g. lower alkyl or aralkyl chlorides, bromides, iodides, lower alkyl alkane- or benzenesulfonates, e.g. the corresponding mesylate or tosylate, or with corresponding aldehydes or ketones and reducing agents, e.g. formic acid, in order to obtain sec. or tert. amines, respectively. Compounds having a tert. amino group or an N-substituted imino grouping can also be converted into N-oxides, for example, by treating them with oxidation agents, such as hydrogen peroxide, aliphatic or aromatic percarboxylic acids, e.g. peracetic or perbenzoic acid.

Finally, a resulting base can be converted into a corresponding acid addition salt, preferably with the use of a acid or anion exchange preparation, or resulting salts can be converted into the corresponding free bases, for example, with the use of a base, such as metal hydroxide, basic salt, ammonia, amine or cation exchange preparation, e.g. an alkali metal hydroxide or carbonate. Said acid addition salts are preferably those with inorganic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicyclic, 4-aminosalicylic, embonic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfonic acid. These or other salts, for example, the picrates, can also be used for purification of the bases obtained; the bases are converted into salts, the salts are separated and the bases are liberated from the salts. In view of the close relationship between the free compounds and the compounds in the form of their salts whenever a compound is referred to in this context, a corresponding salt is also intended, provided such is possible or appropriate under the circumstances.

Resulting mixtures of isomers can be separated into the single isomers by methods in themselves known, e.g. by fractional distillation, crystallization and/or chromatography.

The invention further includes any variant of the present process in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly those starting materials should be used in the reactions of the invention that lead to the formation of those compounds indicated above as being especially valuable.

The starting materials are new and considered as additional subject matter of the present invention. For example, compounds of the formula V are prepared according to the following formula scheme:

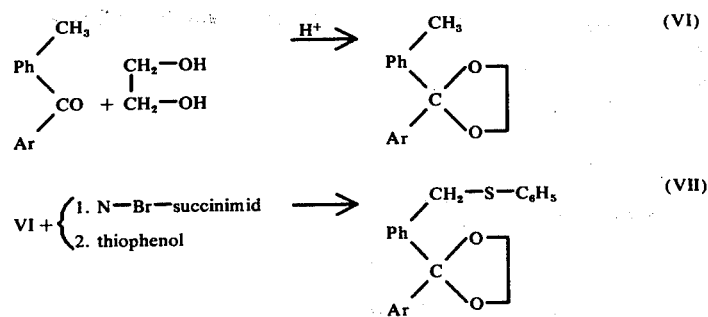

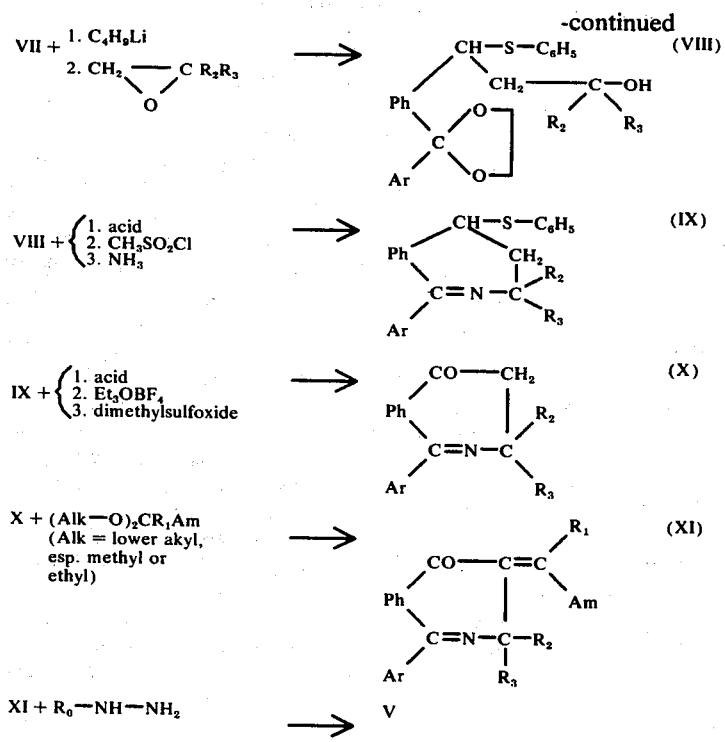

Compounds of Formula XI exhibit the same or similar antianxiety and antidepressant effects as those of I and II.

Another process for preparing the intermediate of the formula VII is the following:

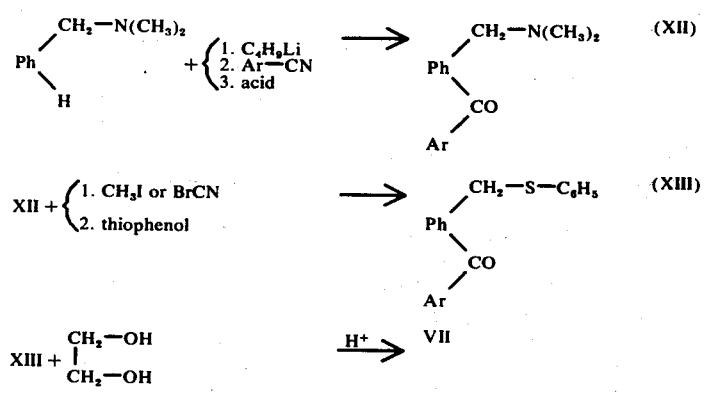

Another version for the manufacture of the starting material of the formula V from the intermediate of the formula X is the following:

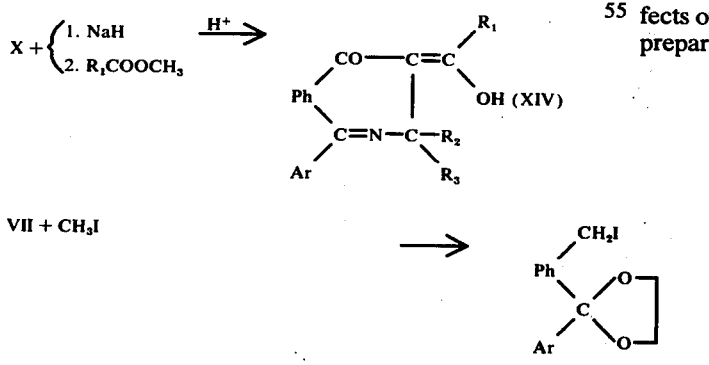

Upon treatment of an intermediate of the formula XIV with an amine H-Am, a compound of the formula XI is obtained.

The starting materials of the formulae Va or Vb, which also exhibit antidepressant and antianxiety effects of the type shown by the compound I or II, can be prepared, for example, as follows:

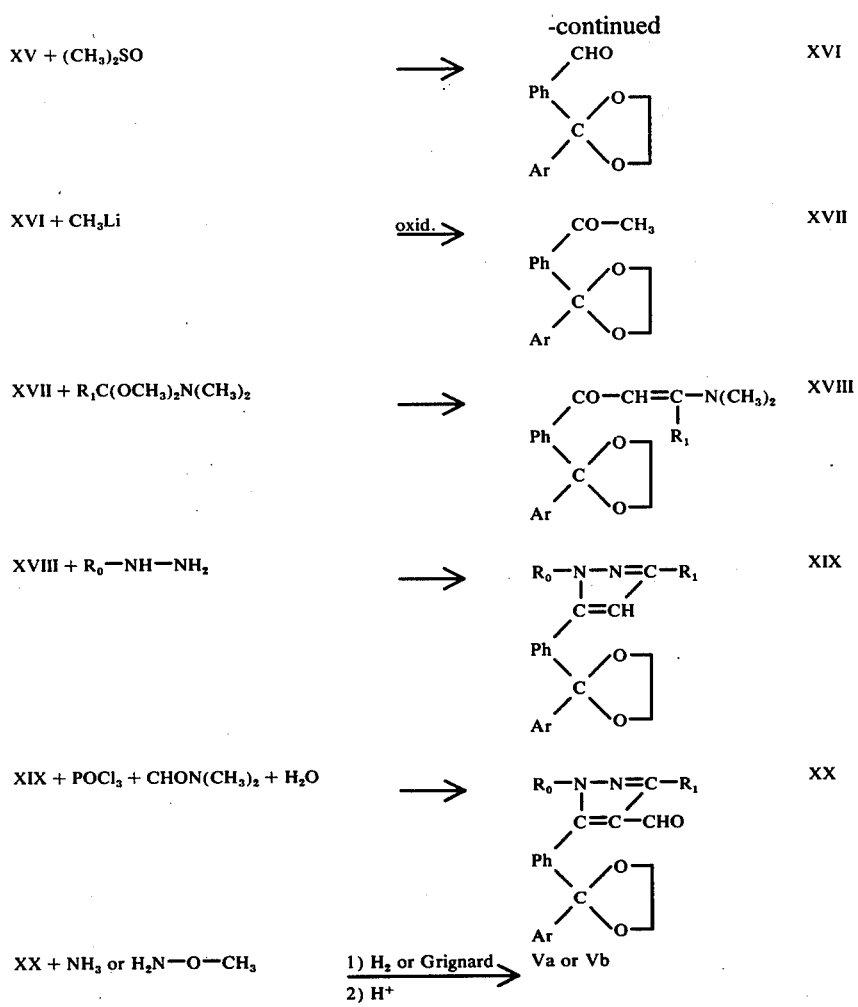
Another version for preparing the starting material of the formula Va or Vb is as follows:
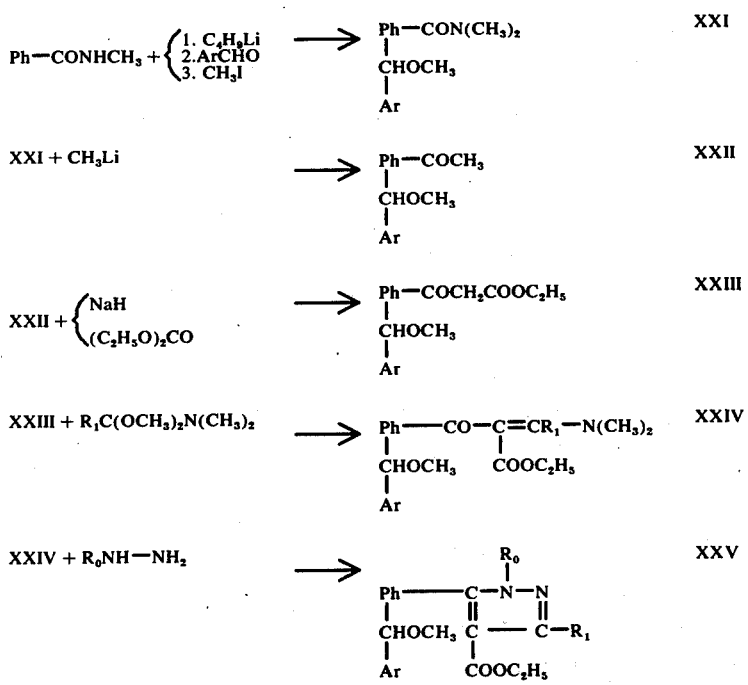

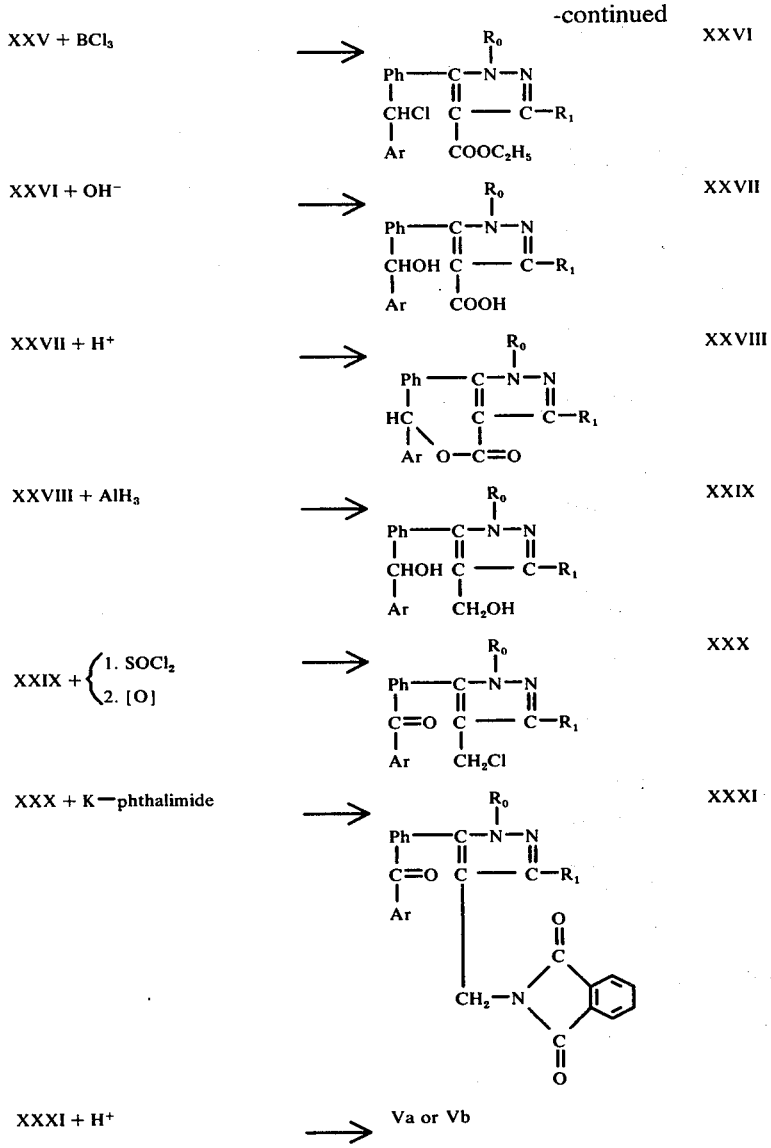
A modification of the above process for the manufacture of the intermediates of the formula XXX from a compound of the formula XXIX may be carried out as follows:
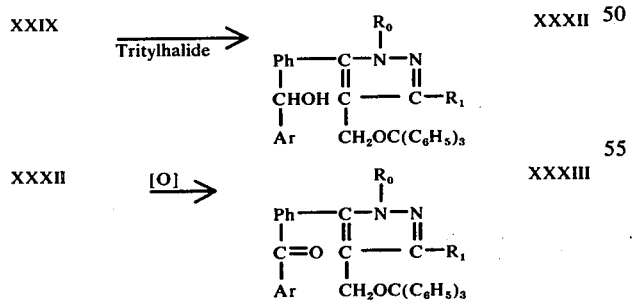
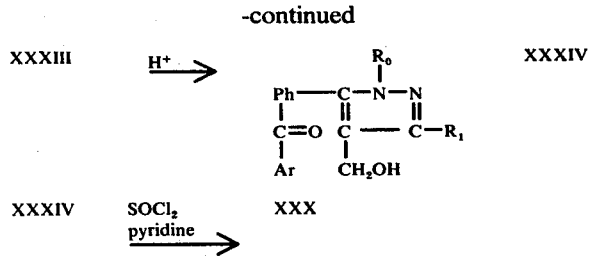
A process for the manufacture of a tautomer of an intermediate of the formula XXXIV, in which $R_0$ is hydrogen, is the following one:
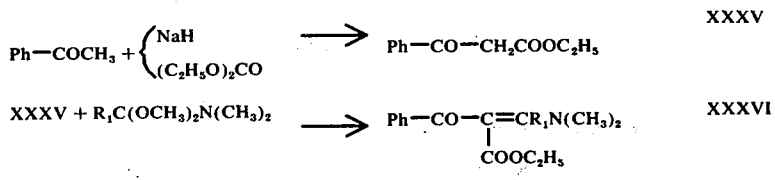

-continued

XXXVI + NH$_2$NH$_2$  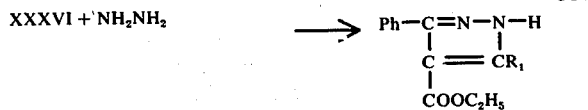  XXXVII

XXXVII + AlH$_3$  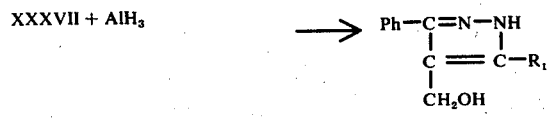  XXXVIII

XXXVIII + H$_2$C=C(CH$_3$)—OCH$_3$  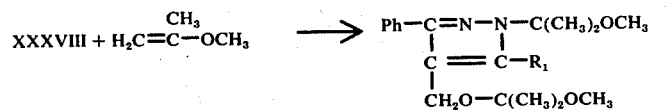  XXXIX

XXXIX {
1. lower alkyl—Li, part. sec-C$_4$H$_9$Li
2. ArCON(R)(R)
(R = alkyl, part. methyl or ethyl)
}  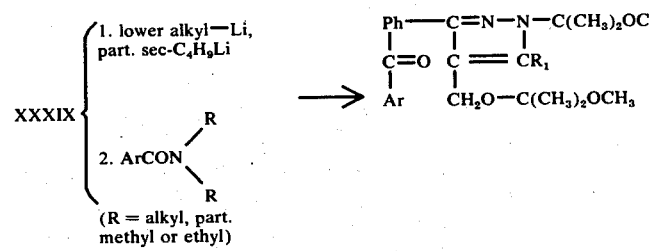  XL XL + H$^+$    XLI In a compound of the formula XLI, the hydrogen attached to the ring-nitrogen may be substituted by any of the organic residues specified for R$_o$; this substitution reaction is carried out as previously shown for compounds of the formulae I or II. In a compound of the formula XL, the imino nitrogen may be quaternized by treatment with a reactive ester of an alcohol, such as a lower alkyl fluorosulfonate, tri-lower alkyl-oxonium tetrafluoroborate and the like, followed by acid hydrolysis, whereby an intermediate of the formula XXXIV is obtained, in which R$_o$ is the residue of an alcohol. Alternatively, a compound of the formula XLI may be treated with a derivative of acrylic acid, such as acrylonitrile or a lower alkyl acrylate, in the N-Michael-addition product the imino nitrogen is then quaternized as previously shown or with another reactive ester of an alcohol, such as a lower alkyl halide, and the quaternary compound is then treated with a base, such as a tertiary amine or an alkali metal hydroxide or lower alkoxide in order to furnish a compound of the formula XXXIV, wherein R$_o$ is the residue of an alcohol.

The starting materials of the formula Vc or Vd, as well as of the formulae Ve or Vf may be obtained as follows:

XXIX + SOCl$_2$  →  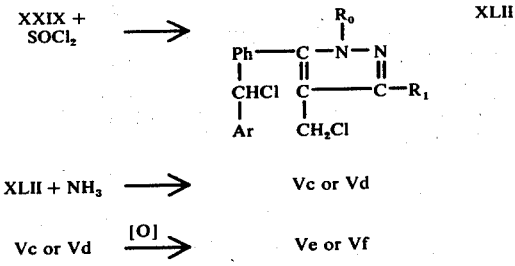  XLII

XLII + NH$_3$ → Vc or Vd

Vc or Vd $\xrightarrow{[O]}$ Ve or Vf

The starting materials of the formulae Va or Vb may also be obtained from the compounds of the formulae I and II, respectively, by treatment of the latter with an acid, such as a mineral acid, for example a hydrohalic, e.g. hydrochloric, or sulfuric or phosphoric acid, in an aqueous medium and, if necessary, in the presence of an organic solvent, such as an alcohol, for example, a lower alkanol, being carried out at room temperature or under cooling at an elevated temperature.

The pharmacologically active compounds of the invention are useful in the manufacture of pharmaceutical compositions containing an effective amount thereof in conjunction of admixture with excipients suitable for either enteral or parenteral application. Preferred are tablets and gelatin capsules comprising the active ingredient together with a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating or coating methods respectively and contain abobut 0.1 to 75%, preferably about 1 to 50% of the active ingredient.

The following examples, illustrating the invention, are not to be construed as being limitations thereon.

Temperatures are given in degrees Centrigrade and all parts wherever given are parts by weight.

EXAMPLE 1

The mixture of 1 g of 8-chloro-4-dimethylaminomethylidene-1-phenyl-3,4-dihydro-2-benzazepin-5-one, 0.33 g of hydrazine hydrate and 45 ml of methanol is refluxed for 4 hours and evaporated under reduced pressure. The residue is taken up in the mainimum amount of acetone-ethanol, the solution acidified with ethereal hydrogen chloride and the precipitate formed filtered off, to yield the 8chloro-6-phenyl-1H,4H-pyrazolo[4,3-d](2) benzazepine dihydrochloride of the formula

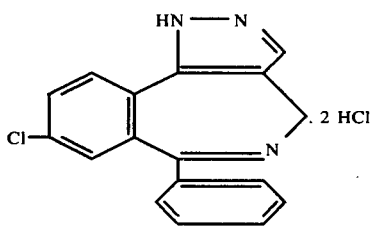

melting at 268° – 270°.

The starting material is prepared as follows: The mixture of 68 g of 5-chloro-2-methylbenzoic acid and 170 ml of thionyl chloride is refluxed for 1 hour, evaporated under reduced pressure and the residual acid chloride dried in a high vacuum. It is taken up in 500 ml of benzene and the solution added dropwise to the suspension of 100 g of anhydrous aluminum chloride and 600 ml of benzene while stirring and cooling with an ice bath. Thereupon the bath is removed and the mixture stirred at room temperature for 16 hours. It is combined with some ice, followed by 340 ml of 2N hydrochloric acid and the mixture stirred for a half hour. It is diluted with diethyl ether, the organic layer separated and washed with 5% sodium hydroxide and saturated aqueous sodium chloride, dried and evaporated under reduced pressure, to yield the 5-chloro-2-methylbenzophenone showing in the I.R. spectrum a strong band at 1660 cm$^{-1}$.

The mixture of 116 g thereof, 2.2 liters of benzene, 5 g of p-toluenesulfonic acid and 120 ml of ethyleneglycol is refluxed on a water separator for 48 hours. Thereupon additional 3 g of p-toluenesulfonic acid are added and refluxing continued for 40 hours. After cooling the mixture in an ice bath, it is washed with ice cold aqueous sodium carbonate, dried, evaporated and the residue crystallized from n-hexane, to yield the corresponding ethylene ketal melting at 76°–77°.

The mixture of 18 g thereof (dried in a high vacuum), 700 ml of carbon tetrachloride, 12.3 g of N-bromosuccinimide and a few crystals of 2,2'-azobis-(2-methyl-propionitrile) is refluxed until all of the N-bromosuccinimide has disappeared. It is cooled, filtered and the filtrate evaporated under reduced pressure. The residue is immediately taken up in 1.1 liters of ice cold methanol and 23.5 ml of thiophenol, immediately followed by 255 ml of N methanolic sodium hydroxide. The mixture is stirred for 20 hours at room temperature, cooled in an ice bath and the precipitate (A) formed filtered off. The filtrate is evaporated under reduced pressure, the residue taken up in diethyl ether, the mixture washed with cold 2N aqueous sodium hydroxide, dried and evaporated. This residue and (A) are combined and crystallized from methanol, to yield the 5-chloro-2-phenylmercaptomethyl-benzophenone ethylene ketal melting at 89°–91°.

To the solution of 51.8 g thereof in 610 ml of dry tetrahydrofuran, 101 ml of 1.6 molar n-butyl lithium in hexane are added while stirring under nitrogen at −67° to −70°. After 1 hour 400 ml of 6 molar ethyleneoxide in tetrahydrofuran are added during 5 minutes, the temperature allowed to rise to −35° and the mixture stirred for two hours at room temperature. It is evaporated under reduced pressure, the residue taken up in 400 ml of dioxane, 400 ml of 2N hydrochloric acid are added and the mixture refluxed for one hour. It is concentrated under reduced pressure to about half its volume, the concentrate extracted with methylene chloride, the extract dried and evaporated, to yield the 5-chloro-2-(3-hydroxy-1-phenylmercaptopropyl)-benzophenone, showing in the NMR spectrum a quartet at $\nu = 4.65$ ppm.

To the mixture of 58.2 g thereof, 28 ml of N,N-diisopropylethylamine and 700 ml of diethyl ether, 21.6 ml of methanesulfonyl chloride are added dropwise while stirring at 0°. After 16 hours the mixture is washed with ice cold 5% hydrochloric acid, ice water and ice cold aqueous sodium carbonate, dried and evaporated under reduced pressure and below 30°. The residual methanesulfonate is taken up in 700 ml of methanol, saturated with ammonia, while stirring and after two hours the solution is again saturated with ammonia. It is allowed to stand at room temperature for 14 days, the precipitate (B) formed filtered off and the filtrate evaporated. The residue is taken up in diethyl ether, the solution extracted with 2N sulfuric acid, the aqueous solution made basic with 30% aqueous sodium hydroxide and extracted with methylene chloride. The extract is dried, evaporated, the residue combined with (B) and recrystallized from methanol, to yield the 8-chloro-1-phenyl-5-phenylmercapto-3,4-dihydro-2-benzazepine melting at 118°–119°.

The solution of 10 g thereof in 100 ml of methylene chloride is neutralized with 5.6 ml of 5.4N ethereal hydrogen chloride and evaporated. The residue is taken up in 100 ml of methylene chloride and 83 ml of molar triethyloxonium tetrafluoro borate in methylene chloride are added while stirring under nitrogen. After 24 hours the mixture is evaporated under reduced pressure, the residue dissolved in 160 ml of dimethylsulfoxide and the solution stirred under nitrogen at 50° for 6 hours. It is evaporated under reduced pressure, the residue taken up in diethyl ether, the solution washed with water and extracted with 5% hydrochloric acid. The pH of the acidic solution is adjusted to 8 with sodium carbonate and the mixture extracted with diethyl ether. The extract is washed with water and saturated aqueous sodium chloride, the washings re-extracted with diethyl ether, the combined extracts dried and evaporated. The residue is taken up in the minimum amount of acetone, the solution neutralized with methanesulfonic acid in acetone and the precipitate formed filtered off, to yield the 8-chloro-1-phenyl-3,4-dihydro-2-benzazepin-5-one methanesulfonate melting at 185°–186°.

It is taken up in water, the solution made basic with aqueous sodium carbonate and extracted with diethyl ether. The extract is dried and evaporated, to yield the corresponding free base.

The mixture of 2.2 g of 8-chloro-1-phenyl-3,4-dihydro-2-benzazepin-5-one and 15 ml of dimethylformamide-dimethylacetal is refluxed for one hour and the excessive reagent removed under reduced pressure at a temperature not exceeding 135°. The residue is crystallized from diethyl ether, to yield the 8-chloro-4-dimethylaminomethylidene-1-phenyl-3,4-dihydro-2-benzazepin-5-one; m.p. 179°–180°.

EXAMPLE 2

The solution of 1.74 g of 8-chloro-6-(2-fluorophenyl)-10a-hydroxy-1-methyl-3a,10a-dihydro-1H,4H-pyrazolo[4,3-d](2)-benzazepine in 60 ml of chloroform is stirred with 100 ml of 0.1 N hydrochloric acid for 15 minutes, the pH of the aqueous phase adjusted to 8 with aqueous sodium carbonate and the mixture again stirred for 5 minutes. The organic layer is separated, dried, evaporated and the residue recrystallized from diethyl ether-hexane, to yield the 8-chloro-6-(2-fluorophenyl)-1-methyl-1H,4H-pyrazolo[4,3-d](2)benzazepine melting at 128°–130°. The corresponding dihydrochloride melts at 190° with decomposition.

The starting material is prepared as follows: The solution of 141 g of α,p-dichlorotoluene in 200 ml of tetrahydrofuran is added dropwise to an ice-cold saturated solution of dimethylamine in 1 liter of tetrahydrofuran and the mixture stirred for 2 days at 25°. It is diluted with diethyl ether, washed with 2N aqueous sodium hydroxide, the organic layer dried, evaporated, the residue distilled and the fraction boiling at 106°/12 mm Hg collected, to yield the N,N-dimethyl-4-chlorobenzylamine.

To the solution of 81.6 g thereof in 1.5 lt of diethyl ether 360 ml of 1.6 molar n-butyl lithium in hexane are added dropwise while stirring at 0°–5° under nitrogen. After 3 hours the solution of 58 g of 2-fluorobenzonitrile in 1.5 lt of diethyl ether is added dropwise while stirring, the mixture refluxed for 3 hours and stirred at room temperature for 16 hours. Thereupon crushed ice and 265 ml of 5N hydrochloric acid are added, the mixture refluxed for ½ hour, coold and the aqueous layer separated. It is made basic for 30% aqueous sodium hydroxide, extracted with methylene chloride, the extract dried, evaporated and the residue dried in a high vacuum at 100°, to yield the 3-chloro-2'-fluoro-6-dimethylaminomethyl-benzophenone melting at 91°–92°.

To the solution of 138 g thereof in 3.2 lt of methylene chloride, that of 55 g of cyanogen bromide in 300 ml of methylene chloride is added dropwise while stirring and cooling with ice. After stirring overnight, the mixture is evaporated under reduced pressure at 40°. The residue is taken up in 2.4 lt of methanol, 56.8 ml of thiophenol are added, followed by 596 ml of N methanolic sodium hydroxide, the mixture stirred for 2 hours at 0° and overnight at room temperature. It is cooled again, filtered and the residue washed with methanol, to yield the 3-chloro-2'-fluoro-6-phenylmercaptomethyl-benzophenone melting at 81°–82°.

The mixture of 144.6 g thereof, 386 g of p-toluenesulfonic acid, 800 ml of ethylene glycol and 3 lt of benzene is refluxed at the water separator for 19 days and evaporated under reduced pressure, to yield the corresponding ethylene ketal melting at 69°.

Said ketal is further processed analogous to the method shown for the 5-chloro-2-phenylmercaptomethyl-benzophenone ethylene ketal in the previous example, to yield the 8-chloro-1-(2-fluorophenyl)-4-dimethylaminomethylidene-3,4-dihydro-2-benzazepin-5-one melting at 224°. (The analogously prepared 2-chlorophenyl- compound melts at 207°).

2 g thereof are added to the solution of 0.7 g of methylhydrazine in 100 ml of ethanol, the mixture refluxed for 45 minutes and evaporated under reduced pressure. The residue is recrystallized from ethyl acetate-hexane, to yield the 8-chloro-6-(2-fluorophenyl)-10a-hydroxy-1-methyl-3a,10a-dihydro-1H,4H-pyrazolo[4,3-d](2)benzazepine melting at 114°–115°.

EXAMPLE 3

The mixture of 0.72 g of 8-chloro-1-(2-chlorophenyl)-4-dimethylaminomethylidene-3,4-dihydro-2-benzazepin-5-one, 0.64 g of benzylhydrazine and 35 ml of ethanol is refluxed for 45 minutes and evaporated under reduced pressure. The residue is taken up in 20 ml methylene chloride, the solution washed with aqueous sodium bicarbonate and stirred with 6 ml of N hydrochloric acid for 20 minutes. The aqueous solution is made basic with sodium carbonate, the mixture stirred, the organic layer separated, dried and evaporated. The residue is taken up in the minimum amount of ethanol, the solution acidified with ethereal hydrogen chloride and the precipitate formed filtered off, to yield the 1-benzyl-8-chloro-6-(2-chlorophenyl)-1H,4H-pyrazolo[4,3-d](2)benzazepine hydrochloride melting at 218°–221°.

EXAMPLE 4

To the solution of 3.3 g of 8-chloro-6-(2-chlorophenyl)-1H,4H-pyrazolo-[4,3-d](2)benzazepine and 50 ml of dimethylformamide, 0.72 g of 57% sodium hydride in mineral oil (washed three times with diethyl ether) are added and the mixture stirred for 30 minutes. Thereupon 1.45 g of methyl iodide in 10 ml of toluene are added and the mixture stirred at room temperature for 16 hours. It is diluted with diethyl ether, washed with water, dried and evaporated. The residue is chromatographed on silica gel and the column eluted with chloroform, to yield a faster moving fraction, yielding after evaporation, the 8-chloro-6-(2-chlorophenyl)-2-methyl-2H,4H-pyrazolo[4,3-d](2)benzazepine of the formula

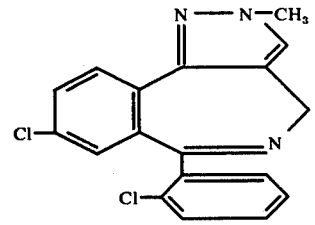

melting at 160°–161°, and a slower moving fraction, yielding the corresponding 1-methyl-isomer, the hydrochloride of which melts at 209°–211°.

EXAMPLE 5

The mixture of 0.33 g of 8-chloro-6-(2-chlorophenyl)-1H,4H-pyrazolo[4,3-d](2)benzazepine, 0.141 g of ethyl chloroformate, 0.16 g of pyridine and 10 ml of methylene chloride is stirred at room temperature for 2 hours. It is diluted with chloroform, washed with aqueous sodium bicarbonate, the organic phase separated, dried and evaporated. The residue is taken up in the minimum amount of acetone and the solution neutralized with ethereal hydrogen chloride, to yield the 8-chloro-6-(2-chlorophenyl)-2-ethoxycarbonyl-2H,4H-pyrazolo[4,3-d](2)benzazepine hydrochloride melting at 151°–152°.

EXAMPLE 6

To the solution of 0.33 g of 8-chloro-6-(2-chlorophenyl) 1H,4H-pyrazolo[4,3-d](2)benzazepine in 10 ml of methylene chloride, the mixture of 0.16 g of dimethylcarbamoyl chloride and 0.15 g of pyridine is added and the whole stirred for 2 hours at room temperature. The mixture is diluted with methylene chloride, washed with ice-cold aqueous sodium carbonate, dried and evaporated under reduced pressure. The residue is chromatographed on silica gel and eluted with benzene-methanol(95:5), to yield the 8-chloro-6-(2-chlorophenyl)-2-dimethylcarbamoyl-2H,4H-pyrazolo[4,3-d](2)benzazepine melting at 175°–176°.

EXAMPLE 7

The solution of 1.45 g of 8-chloro-6-(2-fluorophenyl)-1H,4H-pyrazolo[4,3-d](2)benzazepine and 1.4 ml of methylisocyanate in 20 ml of tetrahydrofuran is refluxed for 5 hours under nitrogen and evaporated under reduced pressure. The residue is taken up in chloroform, the solution filtered through a column of 15 g of silica gel, the first fractions collected, evaporated and the residue recrystallized from diethyl ether, to yield the 8-chloro-6-(2-fluorophenyl)-2-methylcarbamoyl-2H,4H-pyrazolo[4,3-d](2)benzazepine melting at 192°–193°.

EXAMPLE 8

The suspension of 0.5 g of 3-chloro-6-(1-methyl-4-aminomethyl-5-pyrazolyl)-2'-fluorobenzophenone monophosphate in 20 ml of 0.5N aqueous sodium hydroxide and 50 ml of methylene chloride is shaken for 5 min., the organic layer separated, dried and evaporated, to yield the 8-chloro-6-(2-fluorophenyl)-1-methyl-1H,4H-pyrazolo[4,3-d](2)benzazepine melting at 128°; it is identical with that obtained according to Example 2.

The starting material is obtained as follows: The solution of 10 g of 3-chloro-2'-fluoro-6-phenylmercaptomethyl-benzophenone ethylene ketal (Example 2) in 50 ml of methyl iodide is refluxed under nitrogen for 5 days. It is evaporated and the formed methyl phenyl thioether distilled off at 60°/0.1 mm Hg. to yield the 3-chloro-2'-fluoro-6-iodomethyl-benzophenone ethylene ketal.

The mixture of 9.6 g thereof, 5 g of sodium bicarbonate and 50 ml of dimethylsulfoxide is stirred for 20 minutes at 110°, coold and poured onto ice. The mixture is extracted with diethyl ether, the extract washed with water and saturated aqueous sodium chloride, dried, evaporated and the residue recyrstallized from diethyl ether-hexane, to yield the 3-chloro-2'-fluoro-6-formylbenzophenonone ethylene ketal melting at 103°–105°.

To the solution of 1.6 g thereof in 60 ml of diethyl ether, 3 ml of 2.3 molar methyl lithium in diethyl ether are added while stirring and cooling with ice. After 5 minutes 20 ml of water are added cauteously, the organic layer separated, washed with saturated aqueous sodium chloride, dried and evaporated, to yield the 3-chloro-2'-fluoro-6-(1-hydroxy-ethyl)-benzophenone ethylene ketal showing in the NMR-spectrum a doublet at $\nu$=1.1 ppm (in deuterochloroform).

To the solution of 1.8 g thereof in 100 ml of diethyl ether, 25 ml of the solution (obtained from 100 g of sodium dichromate dihydrate, 300 ml of water, 136 ml of concentrated sulfuric acid and diluting it with water to 500 ml) are added while stirring. After 40 minutes the mixture is poured on ice, the organic phase separated and washed with aqueous sodium bisulfite, water, aqueous sodium bicarbonate and saturated aqueous sodium chloride. It is dried and evaporated, to yield the 6-acetyl-3-chloro-2'-fluorobenzophenone ethylene ketal showing in the NMR spectrum a singlet at $\nu$=2.4 ppm.

The mixture of 1.1 g thereof and 7 ml of dimethyl formamide dimethylacetal is refluxed for 16 hours and evaporated under reduced pressure, to yield the 3-chloro-6-(3-dimethylaminoacryloyl)2'-fluoro-benzophenone ethylene ketal showing in the NMR-spectrum a broad singlet at $\nu$=2.7 ppm.

The mixture of 1.3 g thereof, 0.3 g of methylhydrazine and 25 ml of ethanol is refluxed for 7 hours under nitrogen and evaporated. The residue is chromatographed on silica gel and the column eluted first with benzene, then diethyl ether and the ether eluate collected, to yield the 3-chloro-2'-fluoro-6-(1-methyl-5-pyrazolyl)-benzophenone ethylene ketal showing in the NMR-spectrum a singlet at $\nu$=3.1 and a doublet at 84 =5.95 ppm.

The solution of 650 mg thereof in 2.7 ml of ethylene dichloride is added dropwise to the complex, prepared from 265 mg of dimethylformamide and 555 mg of phosphorus oxychloride, while cooling with ice, and dissolved in 1.8 ml of ethylene dichloride, while stirring and the mixture is refluxed for 2 hours under nitrogen. After cooling the solution of 2.45 g of sodium acetate trihydrate in 3.6 ml of water is added and the mixture refluxed for 15 minutes. It is diluted with methylene chloride and water, the organic layer separated and dried, to yield the 3-chloro-2'-fluoro-6-(1-methyl-4-formyl-5-pyrazolyl)-benzophenone ethylene ketal, showing in the NMR-spectrum a band at $\nu$=9.13 ppm.

The mixture of 660 mg thereof, 3 ml of pyridine and 170 mg of O-methyl-hyroxylamine hydrochloride is stirred for 16 hours at room temperature and evaporated under reduced pressure. The residue is taken up in chloroform and the solution filtered through a short column of silica gel, to yield the corresponding methoxime.

The mixture of 130 mg thereof, 25 ml of diethyl ether and 100 mg of lithium aluminum hydride is stirred at room temperature for 16 hours. Thereupon 0.1 ml of water, 0.1 ml of 15% aqueous sodium hydroxide and 0.3 ml of water are added, the mixture filtered and the filtrate extracted with N hydrochloric acid. The acidic layer is separated, made basic with 2N aqueous sodium hydroxide, extracted with methylene chloride, the extract dried and evaporated, to yield the 3-chloro-6-(1-methyl-4-aminomethyl-5-pyrazolyl)-2'-fluorobenzophenone ethylene ketal, showing in the NMR-spectrum a singlet at $\nu$=3.03 and a triplet at $\nu$=8.0 ppm.

The mixture of 100 mg thereof, 10 ml of dioxane and 10 ml of 2N hydrochloric acid is refluxed for 1 hour under nitrogen and the dioxane evaporated. The aqueous solution is cooled, admixed to methylene chloride, made basic with 2N aqueous sodium hydroxide and extracted with diethyl ether. The extract is dried, filtered into the solution of 50 mg of phosphoric acid in 1 ml of ethanol and the precipitate filtered off, to yield the 3-chloro-6-(1-methyl-4-aminomethyl-5-pyrazolyl)-

2'-fluorobenzophenone monophosphate melting at 180°.

EXAMPLE 9

According to the methods illustrated by the previous examples, the following compounds of Formulae III and IV are prepared from equivalent amounts of the corresponding starting materials: $R_6 = Cl$, $R_3 = H$

| No. | $R_4$ | $R_5$ | $R_7$ | Salt | m.p.° C |
|---|---|---|---|---|---|
| 1 | H | H | — | $CH_3SO_3H$ | 221 |
| 2 | $CH_3$ | H | — | 2HCl | 255 |
| 3 | H | F | — | '' | 225(dec.) |
| 4 | $n-C_3H_7$ | F | — | '' | 199 |
| 5 | H | Cl | — | HCl | 220(dec.) |
| 6 | $(CH_2)_2N(C_2H_5)_2$ | F | — | cyclamate | 105(dec.) |
| 7 | $(CH_2)_2N(C_2H_5)_2$ | Cl | — | 2 HCl | 195(dec.) |
| 8 | $(CH_2)_2OH$ | F | — | HCl | 169 |
| 9 | $(CH_2)_3N(C_2H_5)_2$ | F | — | cyclamate | 110(dec.) |
| 10 | — | F | $CH_3$ | — | 139 |
| 11 | — | F | $CO_2C_2H_5$ | HCl | 168 |
| 12 | — | Cl | $CONH-CH_3$ | — | 192 |
| 13 | — | F | $CON(CH_3)_2$ | — | 170 |
| 14 | — | Cl | $CSNH-CH_3$ | — | 195 |

EXAMPLE 10

Preparation of 10,000 tablets each containing 25 mg of the active ingredient:

| Formula: | |
|---|---|
| 8-chloro-6-(2-fluorophenyl)-1-methyl-1H,4H-pyrazolo-[4,3-d](2)benzazepine dihydrochloride | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

PROCEDURE

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 10 mg of the active ingredient:

| Formula: | |
|---|---|
| 8-chloro-6-(2-fluorophenyl)-1-methyl-1H,4H-pyrazolo-[4,3-](2)benzazepine | 500.0 g |
| Lactose | 2,350.0 g |
| Talcum powder | 150.0 g |

PROCEDURE

All the powders are passed through a screen with openings at 0.6 mm. Then the drug substance is placed in a suitable mixer and mixed first with the talcum, then with the lactose until homogenous. No. 2 capsules are filled with 300 mg of the mixture, using a capsule filling machine.

EXAMPLE 11

The mixture of 450 mg of 3,2'-dichloro-6-(1-t. butyl-4-formyl-3-pyrazolyl)-benzophenone, 400 mg of anhydrous sodium sulfate and 10 ml of saturated methanolic ammonia is stirred at room temperature for 3 days. It is evaporated, the residue taken up in methylene chloride, the solution washed with aqeuous sodium bicarbonate, dried and evaporated, to yield the 8-chloro-6-(2-chlorophenyl-4-hydroxy-2-t. butyl-2H,4H-pyrazolo [4,3-d](2)benzazepine, showing in the NMR-spectrum bands at $\nu$—4.92 and 1.44 ppm.

The starting material is prepared as follows: To the solution of 17 g of potassium t-butoxide in 150 ml of ethyleneglycol. 24 g of 4-chlorophenyl propargylketone are added portionwise while stirring at 0°. After one hour 9 g of acetic acid are added, the mixture poured onto ice, diluted with diethyl ether and the pH thereof adjusted to 8 with sodium bicarbonate. The ethereal layer is separated, washed with saturated aqueous sodium chloride, dried and evaporated, to yield the 2-(4-chlorobenzoyl)-acetaldehyde ethylene acetal.

The mixture of 11.9 g thereof, 11.73 g of pyridinium chloride, 8.97 g of t. butylhydrazine and 76 ml of pyridine is stirred at 80° for 23 hours and evaporated under reduced pressure. The residue is taken up in methylene chloride the solution washed with aqueous sodium bicarbonate, dried, evaporated and the residue recrystallized from hot hexane, to yield the 1-t, butyl-3-(4-chlorophenyl)-pyrazole melting at 62°.

The solution of 700 mg thereof in 25 ml of diethyl ether and 2.2 ml of 1.6 molar n-butyl lithium in hexane is stirred at 0° for one hour. Thereupon the solution of 480 mg of 2-chlorobenzonitrile in 10 ml of diethyl ether is added and the mixture stirred for 5½ hours at room temperature. It is diluted with 30 ml of water, extracted with diethyl ether, the extract washed with saturated aqueous sodium chloride and evaporated under reduced pressure. The residue is taken up in 20 ml of methanol and 5 ml of N hydrochloric acid, the solution refluxed for two hours concentrated, the concentrate diluted with methylene chloride and neutralized with sodium carbonate. The organic layer is separated, dried, concentrated and the precipitate collected, to yield the 3,2'-dichloro-6-(1-t. butyl-3-pyrazolyl)-benzophenone, melting at 105°–107°.

To the solution of 370 mg thereof in 1.5 ml of ethylene chloride, that of the complex, obtained from 146 mg of dimethylformamide and 306 mg of phosphorus oxychloride at 0°, in 1 ml of ethylene chloride is added and the mixture refluxed for 2 hours. Thereupon the solution os 1.35 g of sodium acetate trihydrate in 2 ml of water is added, refluxing continued for 15 minutes, the mixture cooled and diluted with methylene chloride and water. The organic layer is separated, dried and evaporated, to yield the 3,2'-dichloro-6-(1-t. butyl-4-formyl-3-pyrazolyl)-benzophenone, showing in the NMR-spectrum ban ds at $\delta$=9.63, 7.95 and 1.95 ppm.

EXAMPLE 12

According to the analogous method described in the previous examples, the following compounds of Formula XI are prepared from equivalent amounts of the corresponding starting materials:

a. 4-dimethylaminomethylidene-1-phenyl-3,4-dihydro-2-benzazepin-5-one, m.p. 134°–136° (methanesulfonate m.p. 185°–187°);
b. 8-chloro-4-dimethylaminomethylidene-1-(2-fluoro or chlorophenyl)-3,4-dihydro-2-benzazepin-5-one, melting at 224° or 207° respectively.

Other compounds XI can be prepared as follows: The mixture of 1.9 g of 8-chloro-4-hydroxymethylidene-1-phenyl-3,4-dihydro-2-benzazepin-5-one, 30 ml of ethanol and 0.7 g of morpholine is stirred for 16 hours at room temperature and evaporated under reduced pressure. The residue is crystallized from diethyl ether, to yield the c. 8-chloro-4-morpholinomethylidene-1-phenyl-3,4-dihydro-2-benzazepin-5-one, m.p. 144°–146°;

The starting material is prepared as follows: To the solution of 2.6 g of 8-chloro-1-phenyl-3,4-dihydro-2-benzazepin-5-one in 4- ml of diethyl ether, 0.5 g of sodium hydride in 10 ml of diethyl ether are added and the mixture stirred for ½ hour. Thereupon 1.2 ml of ethyl formate and 0.1 ml of ethanol are added and the mixture refluxed for 24 hours. It is cooled in an ice bath, 30 ml of water are added, the aqueous layer separated, acidified with 2N hydrochloric acid and the precipitate formed filtered off, to yield the 8-chloro-4-hydroxymethylidene-1-phenyl-3,4-dihydro-2-benzazepin-5-one hydrochloride melting at 185° with decomposition.

It can also be obtained by hydrolyzing 2.1 g of the 8-chloro-4-dimethylaminomethylidene-1-phenyl-3,4-dihydro-2-benzazepin-5-one with 5- ml of 2N hydrochloric acid at 25° for 2 hours while stirring. The precipitate formed is filtered off to yield said hydrochloride melting at 185° with decomposition. It is taken up in water, the pH of the solution adjusted to 7.5 with aqueous sodium carbonate, extracted with methylene chloride, the extract dried and evaporated, to yield said starting material melting at 131°–132°.

In the analogous manner these other compounds are prepared.

d. 8-chloro-4-(methylamino- or 3-hydroxy-propylamino-methylidene-1-phenyl-3,4-dihydro-2-benzazepin-5-one, melting at 176° and 205° (dec.) respectively;
e. 8-chloro-4-methylaminomethylidene-1-(2-fluoro- or 2-chlorophenyl)-3,4-dihydro-2-benzazepin-5-one hydrochloride, melting at 225° and 210° (dec.) respectively.

Tablets or capsules of these compounds are prepared analogous to Example 10.

EXAMPLE 13

A solution of 0.208 g of 3-[4-chloro-2-(2-fluoro-benzoyl)-phenyl]-2-methyl-4-phthalimidomethyl-pyrazole in 2 ml of concentrated hydrochloric acid and 2 ml of water is refluxed for 16 hours under an atmosphere of nitrogen. The solution is cooled with ice, made alkaline by adding a 15% aqueous sodium hydroxide solution and the product is extracted with methylene chloride. The organic layer is dried over anhydrous sodium sulfate and the solvent is evaporated to give a residue consisting of a mixture of 8-chloro-6-(2-fluoro-phenyl)-1-methyl-1H-pyrazolo[4,3-d](2)benzazepine and mainly of the 4-aminomethyl-3-[4-chloro-2-(2-fluoro-benzoyl)-phenyl-2-methyl-pyrazole. By dissolving the residue in ethanol and warming it on a steam bath for about one hour, the latter is converted to the desired 8-chloro-6-(2-fluoro-phenyl)-1-methyl-1H,4H-pyrazolo[4,3-d](2)benzazepine, which is purified by recrystallization from diethyl ether or from cyclohexane to give analytically pure material, ,.p. 126°–128°.

The starting material is prepared as follows: To a mixture of 1250 ml of a 40% aqueous solution of methylamine and 1250 ml of methylene chloride, cooled in an ice bath, is added with stirring a solution of 500 g of 4-chlorobenzoylchloride in 625 ml of methylene chloride. After the addition (50 minutes), the mixture is stirred for an additional 2 hour. The white precipitate is filtered off and air dried and the methylene chloride layer of the filtrate is dried and evaporated to give the crude 4-chloro-N-methyl-benzamide, which, after crystallization from 1200 ml of methanol melts at 158°–161°; an additional amount of the product is recovered from the mother liquor, m.p. 158°–160°.

In a 3-necked flask equipped with thermometer, nitrogen inlet and dropping funnel, 84.75 g of 4-chloro-N-methylbenzamide is dissolved in 3000 ml of dry tetrahydrofuran and cooled to −45° while stirring under a nitrogen atmosphere. When this temperature is reached, 660 ml of a 1.6 molar solution of n-butyl-lithium in hexane are added at such a rate, that the temperature does not exceed −40°. After the addition is complete, the cooling bath is removed and the temperature is allowed to raise to +10°. The mixture is then cooled in an ice bath and 65.6 g of 2-fluoro-benzaldehyde in 100 ml of tetrahydrofuran is added in one batch. The bath is removed and the mixture is then stirred at room temperature for 2¼ hours; the pinkish color of the precipitate changes to a light grey. The flask is cooled again, 160 ml of methyl iodide is added and the reaction mixture is stirred at room temperature for 68 hours. The tetrahydrofuran is then removed under reduced pressure, the residue is taken up in about 1000 ml of diethyl ether and shaken with a mixture of ice and water. After separation, the organic layer is washed with a saturated aqueous sodium chloride solution and dried over anhydrous sodium sulfate. The aqueous layers are reextracted with an additional portion of diethyl ether. Removal of the solvent leaves the 4-chloro-2-(2-fluoro-α-methoxybenzyl)-N,N-dimethyl-benzamide as an oily residue, which is directly used in the subsequent step.

A solution of 142 g of the dry 4-chloro-2-(2-fluoro-α-methoxy-benzyl)-N,N-dimethyl-benzamide in 1400 ml of toluene is cooled to −45° under an atmosphere of nitrogen. Then, a solution of 780 ml of a 1.7 molar solution of methyl lithium in diethyl ether is added at a rapid rate but without allowing the temperature to exceed −40°. The temperature is then allowed to slowly raise to room temperature. One hour after the addition of the methyl lithium, the reaction is quenched with ice/water, the organic layer is separated, washed with a saturated aqueous solution of sodium chloride and dried over anhydrous sodium sulfate. The aqueous layers are reextracted with diethyl ether. After evaporation of all solvents, the residue is crystallized from hexane to give the 4-chloro-2-(2-fluoro-α-methoxy-benzyl)-acetophenone, m.p. 59°–61°.

A solution of 85.3 g of the 4-chloro-2-(2-fluoro-α-methoxy-benzyl)-acetophenone in 370 ml of diethyl carbonate is added to a cooled (ice bath) suspension of 17.2 g of sodium hydride (55% in mineral oil, washed with diethyl ether to free it from the mineral oil) in 180 ml of diethyl carbonate. After the addition, the reaction mixture is stirred at room temperature for 2½ days, then diluted with diethyl ether. Ice is added and the pH is adjusted to 6 by adding hydrochloric acid and an aqueous sodium dihydrogenphosphate solution. After separation, the organic layer is washed with a saturated aqueous solution of sodium chloride, dried over sodium sulfate and evaporated to dryness. All aqueous layers are reextracted with diethyl ether. The ethyl 3-[4-chloro-2-(2-fluoro-α-methoxy-benzyl)-phenyl]-3-oxo-propionate is obtained as a liquid residue, which is used in the next step without further purification.

A solution of 107 g of the crude ethyl 3-[4-chloro-2-(2-fluoro-α-methoxy-benzyl)-phenyl]-3-oxo-propionate in 200 ml of dry dimethylformamide is refluxed for 1 hour with 84 ml of dimethylformamide-dimethylacetal under an atmosphere of nitrogen. Then, all solvent and excess reagent are removed at a pressure of 12 mm Hg. The residue, consisting of ethyl 3-[4-chloro-2-(2-fluoro-α-methoxy-benzyl)-2-dimethylaminomethylene-3-oxo-propionate and containing some dimethylformamide, is directly used in the next step.

A solution of 127 g of the crude ethyl 3-[4-chloro-2-(2-fluoro-α-methoxy-benzyl)-2-dimethylaminomethylene-3-oxo-propionate in 1500 ml of ethanol is refluxed for 1 hour with 25 g of methyl hydrazine under an atmosphere of nitrogen. Then, all solvent and volatile reagent are removed at a pressure of 12 mm Hg, and the residue is crystallized from 400 ml of diethyl ether to give product A, m.p. 128°–130°. Charcoal treatment of the mother liquor and evaporation to 150 ml, provides a product B, m.p. 114°–116°. Product A represents one isomeric (rotameric) form of the 3-[4-chloro-2-(2-fluoro-α-methoxy-benzyl)-phenyl]-4-ethoxycarbonyl-2-methyl-pyrazole, whereas product B is primarily the other isomeric (rotameric) form of the product, contaminated with a small amount of the first isomer.

To a solution of 20.1 g of 3-[4-chloro-2-(2-fluoro-α-methoxy-benzyl)-phenyl]-4-ethoxycarbonyl-2-methyl-pyrazole in 250 ml methylene chloride is added 54 ml of a 1.4 molar boron trichloride solution in methylene chloride, and the mixture is stirred during 16 hours. Ice/water is then added; the organic layer separated, washed with a saturated solution of sodium chloride and dried over anhydrous sodium sulfate. The aqueous layers are reextracted with methylene chloride. After removal of the solvent, the 3-[4-chloro-2-(α-chloro-2-fluoro-benzyl)-phenyl]-4-ethoxycarbonyl-2-methyl-pyrazole is obtained as the solid residue, which is directly used in the next step.

A solution of the 3-[4-chloro-2-(α-chloro-2-fluoro-benzyl)-phenyl]4-ethoxycarbonyl-2-methyl-pyrazole in 200 ml of dioxane is refluxed for 4 hours with 75 ml of a 2H aqueous solution of sodium hydroxide. The mixture is evaporated, the residue is shaken between diethyl ether and water, the basic aqueous layer is separated and acidified with 35 ml of 5H hydrochloric acid and extracted twice with methylene chloride. Drying of the organic layer over anhydrous sodium sulfate and evaporation of the solvent produces a foamy residue, comprising the 4-carboxy-3-[4-chloro-2-(2-fluoro-α-hydroxy-benzyl)-phenyl]-2-methyl-pyrazole, which is directly used in the subsequent step.

A solution of 20.3 g of the crude 4-carboxy-3-[4-chloro-2-(2-fluoro-α-hydroxy-benzyl)-phenyl]-2-methyl-pyrazole in 500 ml of toluene is refluxed with 1 g of p-toluenesulfonic acid using a water separator for 16 hours while stirring; the starting material starts to precipitate at the beginning but redissolves on further refluxing. The mixture is cooled, the toluene is evaporated using a rotary distillation apparatus until a product starts to precipitate. The mixture is then cooled, and a first crop of 8-chloro-6-(2-fluoro-phenyl)-1-methyl-4-oxo-1H,6H-pyrazolo[4,3-d](2)benzoxepine, m.p. 198°–200°, can be collected. The mother liquor is washed with a cold aqueous solution of sodium carbonate, dried and evaporated. Crystallization of the residue from a mixture of diethyl ether and toluene provides an additional crop of the product, m.p. 219°–220°.

The aluminum hydride used in the following step is prepared according to the procedure described by Brown et al, J. Am. Chem. Soc., Vol. 90, page 2934 (1968): a mixture of 3.05 g of lithium aluminum hydride in 52 ml of dry tetrahydrofuran is stirred for 2 hours at room temperature. An additional 68 ml of tetrahydrofuran are added. The mixture is cooled in an ice bath and then treated with 2.14 ml of concentrated sulfuric acid, which is added dropwise. Vigorous stirring is continued for one hour at room temperature. The supernatant solution of the aluminum hydride is directly used in the following reaction.

To an ice-cooled solution of approximately 33 m moles of aluminum hydride in 50 ml of tetrahydrofuran is added a solution of 6.86 g of 8-chloro-6-(2-fluoro-phenyl)-1-methyl-4-oxo-1H,6H-pyrazolo[4,3-d](2)benzoxepine in 150 ml of dry tetrahydrofuran under an atmosphere of nitrogen. After the addition, the mixture is stirred an additional 30 minutes in an ice bath. The excess of the reagent is then carefully destroyed by adding water; 50 ml of 2N hydrochloric acid is added to dissolve the voluminous precipitate. The two layers are separated, the organic layer is washed with a saturated aqueous sodium chloride solution and dried over anhydrous sodium sulfate. All aqueous layers are reextracted with diethyl ether. The residue (consisting of a mixture of thermally interconvertible isomers) is taken up in 100 ml of dioxane and refluxed for 2 hours. The dioxane is then removed under reduced pressure and the residue is crystallized from 30 ml of diethyl ether to give the thermodynamically more stable isomer of the 3-[4-chloro-2-(2-fluoro-α-hydroxy-benzyl)-phenyl]-4-hydroxymethyl-2-methyl-pyrazole, m.p. 152°–155°. The mother liquor is equilibriated again by refluxing in dioxane and an additional amount of the product, m.p. 153°–155°, can be collected.

A solution of 1.04 g of 3-[4-chloro-2-(2-fluoro-α-hydroxybenzyl)-phenyl]-4-hydroxymethyl-2-methyl-pyrazole in 25 ml of anhydrous tetrahydrofuran is cooled in a dry nitrogen atmosphere in an ice bath. Then, 7.15 ml of a 0.504 molar solution of thionyl chloride in benzene is added through a dropping funnel, followed by 7.25 ml of a 0.496 molar solution of pyridine in tetrahydrofuran. After the addition, a precipitate forms, the mixture is stirred for 30 minutes in the ice bath and is then treated with 20 ml of 4N aqueous sulfuric acid. The mixture is stirred for another 30 minutes in the ice bath. The two layers are then separated in a separatory funnel, washed with a concentrated solution of sodium chloride and the aqueous layers are reextracted with diethyl ether. After drying the organic layers, the solvent is removed at a temperature of below 35°.

The residue is then dissolved in 50 ml of diethyl ether, cooled in an ice bath and 5 ml of an aqueous chromic acid solution (which is prepared by dissolving 100 g of sodium dichromate dihydrate in 300 ml of water, adding 136 ml of concentrated sulfuric acid and diluting the mixture to a volume of 500 ml with water) are added while stirring. After stirring for 30 minutes at 0°, the excess of the chromic acid is destroyed with an aqueous sodium sulfite solution. The mixture is diluted with diethyl ether, transferred to a separatory funnel and the two layers are separated. After washing with water, reextraction of the aqueous layers with diethyl ether and drying over anhydrous sodium sulfate, the solvent is removed on the rotary still below 35° to give the 4-chloromethyl-3-[4-chloro-2-(2-fluoro-benzoyl)-phenyl-1-methyl-pyrazole, which is directly used in the next step.

A solution of 1.0 g of the crude 4-chloromethyl-3-[4-chloro-2-(2-fluoro-benzoyl)-phenyl]-2-methyl-pyrazole in 15 ml of dry dimethylformamide is stirred at room temperature with 0.55 g of potassium phthalimide for 16 hours. The mixture is diluted with diethyl ether, washed twice with water and then with a saturated aqueous sodium chloride solution. The aqueous layers are reextracted with diethyl ether; the organic phase is dried over anhydrous sodium sulfate. After evaporation of the solvent, the residue is dissolved in 15 ml of diethyl ether, whereupon the product crystallizes. A first crop of the 3-[4-chloro-2-(2-fluoro-benzoyl)-phenyl]-2-methyl-4-phthalimidomethyl-pyrazole, m.p. 153°–155°, can be collected.

EXAMPLE 14

A solution of 0.33 g of 3-[4-chloro-2-(2-fluoro-benzoyl)-phenyl]-4-phthalimidomethyl-2-methyl-pyrazole in 20 ml of methanol is saturated with ammonia and allowed to stand at room temperature for 2 days. The residue obtained after removal of solvent is treated with water and then extracted with diethyl ether. The ether extract is washed with a diluted aqueous sodium hydroxide solution, water and a saturated solution of sodium chloride in water and dried over sodium sulfate. Removal of ether yields an oil which is then chromatographed on a column of silica gel, the material being eluted with ethyl acetate. The solid residue obtained after removal of ethyl acetate is crystallized from a mixture of ethyl acetate and petroleum ether to yield the 8-chloro-6-(2-fluorophenyl)-1-methyl-1H,4H-pyrazolo [4,3-d](2) benzazepine m.p. 127°–129°, which is identical with the compound prepared according to the process of example 2.

The starting material is prepared as follows: A solution of 0.347 g of 3-[4-chloro-2-(2-fluoro-α-hydroxy-benzyl)-phenyl]-4-hydroxymethyl-2-methyl-pyrazole, 0.278 g of trityl chloride and 0.101 g of triethylamine in 15 ml of methylene chloride stirred for 16 hours at room temperature. The solution is then filtered through a small column of neutral aluminum oxide. The column is washed with methylene chloride and the filtrate, containing the 3-[4-chloro-2-(2-fluoro-α-hydroxy-benzyl)-phenyl]-2-methyl-4-trityloxymethyl-pyrazole, is used in the next step.

The above solution is added to a solution of 0.6 g of chromium trioxide and 0.95 g of pyridine in 15 ml of methylene chloride. After 15 minutes the solution is filtered through a small column of neutral aluminum oxide; the column washed with methylene chloride and the filtrate is evaporated to dryness. Toluene is added to the residue which contains some pyridine. The toluene is removed by evaporation under reduced pressure and the residue, containing the 3-[4-chloro-2-(2-fluoro-benzoyl)-phenyl]2-methyl-4-trityloxymethyl-pyrazole, is used without any further purification in the next step.

The above residue is dissolved in 15 ml of tetrahydrofuran and 4 ml of concentrated hydrochloric acid is added to the solution, which is then stirred for three hours at room temperature. The solvent is removed by evaporation under reduced pressure and the residue is treated with diethyl ether and a saturated solution of sodium bicarbonate. The ether solution is washed with water, dried over sodium sulfate and passed through a column of silica gel; the triphenyl carbinol is not retained on the column. After washing with diethyl ether, the column is eluted with tetrahydrofuran. The solvent is removed by evaporation to give the 3-[4-chloro-2-(2-fluoro-benzoyl)-phenyl]-4-hydroxymethyl-2-methyl-pyrazole as a colorless oil.

Alternatively, the 3-[4-chloro-2-(2-fluoro-benzoyl)-phenyl]-2-methyl-4-trityloxymethyl-pyrazole may be dissolved in acetic acid and treated with hydrogen bromide whereupon the trityl bromide is precipitated (and can be reused for tritylation) and the 3-[4-chloro-2-(2-fluoro-benzoyl)-phenyl]-4-hydroxymethyl-2-methyl-pyrazole will remain in the acetic acid solution.

To a solution of 0.295 g of the above keto alcohol in 15 ml of tetrahydrofuran is added 0.230 g of thionyl chloride in 5 ml of tetrahydrofuran, followed by 0.160 g of pyridine in 5 ml of tetrahyrofuran. The mixture is stirred at room temperature for 30 minutes and then treated with 10 ml of 1N hydrochloric acid. The organic phase is isolated, dried and evaporated to dryness yielding the 4-chloromethyl-3-[4-chloro-2-(2-fluoro-benzoyl)phenyl]-2-methyl-pyrazole as a colorless oil.

To a solution of the above chloroketone in 5 ml of dimethylformamide is added in equivalent amount of potassium phthalimide. The mixture is stirred for 16 hours at room temperature and then diluted with diethyl ether. The organic solution is then washed with water and saturated aqueous solution of sodium chloride. After drying over sodium sulfate, the ether solution is evaporated to dryness. The oily residue is crystallized from diethylether to yield the 3-[4-chloro-2-(2-fluoro-benzoyl)-phenyl]4-phthalimidomethyl-2-methyl-pyrazole, m.p. 153°-155°.

EXAMPLE 15

A solution of 0.2 g of 8-chloro-6-(2-fluoro-phenyl)-1-methyl-1,4,5,6-tetrahydro-pyrazolo[4,3-d](2) benzazepine in 20 ml of methylene chloride is vigorously stirred with 2 g of manganese dioxide for 22 hours at room temperature. The manganese dioxide is then filtered off, the filtrate is evaporated and the resulting residue, consisting of a mixture of the 8-chloro-6-(2-fluorophenyl)-1-methyl-1H,4H-pyrazolo[4,3d](2) benzazepine and the corresponding 1H,6H-isomer is chromatographed on silica gel using an 8:2-mixture of chloroform and ethyl acetate as the eluate; the 1H, 4-H-compound melts at 128°, the 1H-6H-compound at 163°–165°.

The starting material is prepared as follows: A mixture of 3-[4-chloro-2-(2-fluoro-α-hydroxy-benzyl)-phenyl)-4-hydroxymethyl-2-methyl-pyrazole and 4 ml of thionyl chloride is refluxed for one hour and then evaporated under reduced pressure. The amorphous residue, containing the 4-chloromethyl-3-[4-chloro-2-(2-fluoro-α-chloro-benzyl)-phenyl]-2-methyl-pyrazole, is dissolved in 50 ml of a saturated solution of ammonia in methanol and stirred for 24 hours at room temperature. The mixture is evaporated under reduced pressure, the residue is taken up in methylene chloride, and the solution is washed with dilute aqueous sodium hydroxide, dried over anhydrous sodium sulfate and evaporated. The residue is dissolved in ethanol, the solution is neutralized by adding anhydrous hydrogen chloride gas and diluted with diethyl ether. The resulting crystalline hydrochloride of 8-chloro-6-(2-fluoro-phenyl)-1-methyl-1,4,5,6-tetrahydro-pyrazolo[4,3-d](2) benzazepine melts at 280°.

EXAMPLE 16

A solution of 0.39 g of 8-chloro-6-(2-fluoro-phenyl)-1-methyl-1H,6H-pyrazolo[4,3-d](2) benzazepine in 10 ml of ethanol, containing 0.12 g of potassium tert.-butoxide is refluxed for 12 hours. The solvent is then removed under reduced pressure, the residue is taken up in methylene chloride and the solution is washed with dilute aqueous sodium hydrogen carbonate. The organic layer is separated, dried over anhydrous sodium sulfate and evaporated under reduced pressure. The residue containing a 9:1-mixture of the starting material and the 8-chloro-6-(2-fluorophenyl)-1-methyl-1H,4H-pyrazolo[4,3-d](2) benzazepine is chromatographed with the use of silica gel and an 8:2-mixture of chloroform and ethyl acetate; the desired 8-chloro-6(2-fluoro-phenyl)-1-methyl-1H,4H-pyrazolo[4,3-d](2) benzazepine melts at 128°.

EXAMPLE 17

A solution of 3.5 g of crude 3-[4-chloro-2-(2-chlorobenzoyl)-phenyl]-4-hydroxymethyl-pyrazole in 25 ml of tetrahydrofuran and 4 ml of anhydrous pyridine is cooled in an ice bath. Then 2.5 ml of methanesulfonyl chloride is added and the mixture is stirred at room temperature for 4 hours. Subsequently, 50 ml of a saturated solution of anhydrous ammonia in methanol is added and the mixture stirred at room temperature for 16 hours. All the solvents are then evaporated under reduced pressure and the residue is taken up in ethylacetate and 1N aqueous hydrochloric acid. The acidic layer is separated, basified with 2N aqueous sodium hydroxide and the product extracted into methylene chloride. After drying the organic layer over anhydrous sodium sulfate and removal of the solvent, an amorphous residue is obtained, containing the 8-chloro-6-(2-chlorophenyl) 1H,4H-pyrazolo[4,3-d](2) benzazepine, identical by thin layer chromatographic and NMR-spectroscopic comparisons with compound No. 5 in Example 9. The hydrochloride salt of the pure compounds melts at 220° with decomposition.

The starting material is prepared as follows: A solution of 96.6 g of 4-chloro acetophenone in 300 ml of diethyl carbonate is added dropwise to a suspension of 34 g sodium hydride (55% in mineral oil, washed twice with diethyl ether) in 400 ml of diethyl carbonate at ice bath temperature, then at room temperature for 2 days. To the dark solution is then added crushed ice and 5N hydrochloric acid to adjust the pH to 6–7. After dilution with diethyl ether, the layers are separated, the organic phase washed with a saturated aqueous sodium chloride solution and then dried over anhydrous sodium sulfate. After removal of the solvents, the oily ethyl 3-(4-chloro-phenyl)-3-oxo-propionate is obtained.

A mixture of 57 g of ethyl 3-(4-chloro-phenyl)-3-oxopropionate and 50 ml of dimethylformamide dimethyl acetal is refluxed in 100 ml of dimethylformamide for 1 hour. Then, all solvent and excess reagent is removed in vacuo to give the ethyl 3-(4-chlorophenyl)-2-dimethylamino-methylene-3-oxo-propionate as a dark oily residue, which is used without further purification.

A mixture of 33 g of the above oil and 10 g of hydrazinehydrate is refluxed in 550 ml of ethanol for 1½ hours. The ethanol is then removed in vacuo, the residue taken-up in ethyl acetate and washed with water, then with a saturated aqueous sodium chloride solution. After drying and evaporating the solvent, the residue is crystallized from a mixture of diethyl ether and hexane to give the 3-(4-chloro-phenyl-4-ethoxycarbonyl-pyrazole, m.p. 95°–10°.

A solution of 12 g of ethyl-(4-chloro-phenyl-4-ethoxycarbonyl-pyrazole in 150 ml of tetrahydrofuran is cooled in an ice bath. Then 25 ml of a 1 molar solution of aluminum hydride triethylamine complex in benzene is added dropwise. After the addition, the ice bath is removed and the gelatinous mixture stirred at room temperature for 2 ½ hours. Excess reagent is then destroyed by the dropwise addition of water followed by 30 ml of an aqueous 2N solution of sodium hydroxide. The layers are separated, the aqueous phase reextracted with ethyl acetate and the combined organic layers dried over anhydrous sodium sulfate. The recrystallization of the solid residue from hot ethyl acetate gives the 3-(4-chloro-phenyl)-4-hyroxymethyl-pyrazole, m.p. 149°–150°.

A suspension 5.2 g of 3-(4-chloro-phenyl)-4-hydroxymethyl-pyrazole in 45 ml of a 1:1 mixture of 2,2-dimethoxypropane and methyl isopropenyl ether is stirred at room temperature. After the addition of one drop of phosphorous oxychloride, the mixture becomes exothermic. The refluxing is maintained for 30 minutes, and all starting material is dissolved. The mixture is then cooled and poured onto a mixture of ice and sodium bicarbonate, diluted with diethyl ether, shaken and separated. After drying over anhydrous sodium sulfate and removal of the solvent the 3-(4-chloro-phenyl)-1-(2-methoxy-2-propyl)4-(2-methoxy-2-propyloxy)methylpyrazole is obtained as an oily residue.

A solution of 3.2 g of 3-(4-chloro-phenyl-1-(2-methoxy-2-propyl)-4-(2-methoxy-2-propyloxy)-methyl-pyrazole in 60 ml of diethyl ether is cooled under an atmosphere of nitrogen to −70°. Then 10 ml of a 1.2 molar solution of sec-butyl lithium in hexane are added dropwise. After the addition, the mixture is stirred for 5 minutes at −60° to −70°, whereupon 2.2 g of 2-chloro-N,N-dimethylbenzamide in 10 ml of diethyl ether are added. The cooling bath is then removed and the mixture is stirred at room temperature for 12 hours. It is then poured on ice and water, diluted with diethyl ether, and after separation of the layers, the organic phase is washed with a saturated aqueous sodium chloride solution. After drying and removal of the solvent in vacuo a residue, containing the 3-[4-chloro-2-(2-chloro-benzoyl)-phenyl]-1-(2-methoxy-2-propyl)-4-(2-methoxy-2-propyloxy)-methyl-pyrazole, is obtained as a viscous oil. This material is then dissolved in 75 ml of methanol and stirred at 25° for 2 hours with 6 ml of 2N hydrochloric acid. After the evaporation of the methanol, the residue is taken-up in methylene chloride and made basic with an aqueous solution of sodium carbonate. The organic layer is then separated, dried over anhydrous sodium sulfate and evaporated in dryness to give a very viscous residue, containing the 3-[4-chloro-2-(2-chlorobenzoyl)-phenyl]-4-hydroxymethylpyrazole (NMR δ = 4.25 ppm), which is used without further purification.

I claim:

1. A compound of the formula

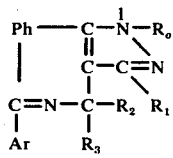

wherein Ph is 1,2-phenylene and Ar is phenyl, both of said radicals are unsubstituted or substituted by one or two, of the same or different substituents selected from the group consisting of lower alkyl, lower alkoxy, halo and trifluoromethyl, $R_o$ is hydrogen, lower alkyl, hydroxy-lower alkyl, lower alkoxylower alkyl, amino-lower alkyl, lower alkylamino-lower alkyl, di-lower alkylamino-lower alkyl, Ar or Ar-lower alkyl, wherein the additional chain-nitrogen or oxygen atom is separated from the ring-nitrogen by at least 2 carbon atoms, each of $R_1$ and $R_2$ is hydrogen or lower alkyl, and $R_3$ is hydrogen, lower alkyl, hydroxy or lower alkanoyloxy; or N-oxides thereof; or pharmaceutically acceptable acid addition salts thereof.

2. A compound as claimed in claim 1, in which formula Ph is 1,2-phenylene, (lower-alkyl)-1,2-phenylene, (lower alkoxy)-1,2-phenylene, (halo)-1,2-phenylene, or (trifluoromethyl)-1,2-phenylene, Ar is H-Ph, $R_o$ is hydrogen, lower alkyl, hydroxy-$C_mH_{2m}$, lower alkoxy-$C_mH_{2m}$, amino-$C_mH_{2m}$, lower alkylamino-$C_mH_{2m}$, di-lower alkylamino-$C_mH_{2m}$ or H-Ph-$C_nH_{2n}$ wherein m is an integer from 2 to 4, and n such from 0 to 4, each of $R_1$ and $R_2$ is hydrogen or lower alkyl, and $R_3$ is hydrogen, lower alkyl, hydroxy or lower alkanoyloxy, or N-oxides thereof, or a pharmaceutically acceptable acid addition salts thereof.

3. A compound as claimed in claim 1, in which formula Ph is 1,2-phenylene, (alkyl)-1,2-phenylene or (halo)-1,2-phenylene, Ar is H-Ph, $R_o$ is hydrogen, alkyl, 2-hydroxyethyl, 2- or 3-hydroxypropyl, 2-dialkylaminoethyl, 2- or 3-dialkylaminopropyl or H-Ph-methyl, each of $R_1$ and $R_2$ is hydrogen or methyl, and $R_3$ is hydrogen or hydroxy, whereby alkyl has 1 to 4 carbon atoms, or a pharmaceutically acceptable acid addition salt thereof.

4. A compound as claimed in claim 3, and corresponding to the formula

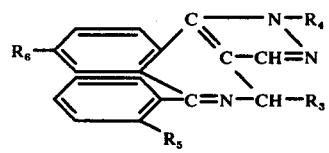

wherein $R_3$ is hydrogen or hydroxy, $R_4$ is hydrogen, alkyl with 1 to 4 carbon atoms, 2-hydroxyethyl, 2- or 3-hydroxypropyl, 2-dimethylaminoethyl, 2- or 3-dimethylaminopropyl, 2-diethylaminoethyl, 2- or 3-diethylaminopropyl or benzyl, and each of $R_5$ and $R_6$ is hydrogen, methyl, fluoro or chloro or a pharmaceutically acceptable acid addition salt thereof.

5. A compound as claimed in claim 4 and being the 8-chloro-6-(2-fluorophenyl)-1-methyl-1H,4H-pyrazolo[4,3-d]-(2) benzazepine or a pharmaceutically acceptable acid addition salt thereof.

* * * * *